(12) United States Patent
Lee et al.

(10) Patent No.: US 8,217,174 B2
(45) Date of Patent: Jul. 10, 2012

(54) METHOD OF PREPARING MONTELUKAST AND INTERMEDIATES USED THEREIN

(75) Inventors: Gwan Sun Lee, Seoul (KR); Young-Kil Chang, Seoul (KR); Jaeheon Lee, Yongin-si (KR); Chul Hyun Park, Seongnam-si (KR); Eun-Ju Park, Seoul (KR); Jaeho Yoo, Seoul (KR)

(73) Assignee: Hanmi Holdings Co., Ltd., Seoul (KR)

( * ) Notice: Subject to any disclaimer, the term of this patent is extended or adjusted under 35 U.S.C. 154(b) by 95 days.

(21) Appl. No.: 12/518,213

(22) PCT Filed: Dec. 11, 2007

(86) PCT No.: PCT/KR2007/006424
§ 371 (c)(1),
(2), (4) Date: Jun. 8, 2009

(87) PCT Pub. No.: WO2008/072872
PCT Pub. Date: Jun. 19, 2008

(65) Prior Publication Data
US 2010/0099876 A1    Apr. 22, 2010

(30) Foreign Application Priority Data
Dec. 14, 2006   (KR) .................. 10-2006-0127942

(51) Int. Cl.
*C07D 215/00* (2006.01)
*C07D 215/18* (2006.01)
*C07F 9/09* (2006.01)
*C07F 9/00* (2006.01)

(52) U.S. Cl. ......................................... 546/23; 546/174

(58) Field of Classification Search .................. None
See application file for complete search history.

(56) References Cited

U.S. PATENT DOCUMENTS
5,614,632 A * 3/1997 Bhupathy et al. ............. 546/180
5,952,347 A   9/1999 Arison et al.

FOREIGN PATENT DOCUMENTS
WO   2005/105751 A1   11/2005
WO   2006/008751 A2   1/2006

OTHER PUBLICATIONS

Smith, M.B., & March, J., March's Advanced Organic Chemistry: Reactions, Mechanisms, & Structure, 5th Ed., Wiley-Interscience Publication, John Wiley & Sons, Chapter 10, p. 464-465 (2001).*

* cited by examiner

*Primary Examiner* — Janet Andres
*Assistant Examiner* — Timothy R Rozof
(74) *Attorney, Agent, or Firm* — Sughrue Mion, PLLC

(57) ABSTRACT

The present invention relates to a method for preparing montelukast, an inhibitor against leukotrienes, and an intermediate used therein. According to the inventive method, high-purity montelukast or its sodium salt can be prepared in a high yield.

11 Claims, No Drawings

METHOD OF PREPARING MONTELUKAST AND INTERMEDIATES USED THEREIN

FIELD OF THE INVENTION

The present invention relates to an improved method for preparing montelukast and an intermediate used therein.

BACKGROUND OF THE INVENTION

Leukotrienes constitute a group of locally functional hormones produced from arachidonic acid in vivo and major leukotrienes include leukotriene B4 (LTB4), C4 (LTC4), D4 (LTD4) and E4 (LTE4). The biosynthesis of the leukotrienes involves the production of an epoxide known as leukotriene A4 (LTA4) from arachidonic acid by the action of 5-lipoxygenase, and LTA4 is then converted to various leukotrienes through a series of enzymatic steps (see Leukotrienes and lipoxygenases, ed. J. Rokach, Elsevier, Amsterdam, 1989).

Recently, montelukast or its pharmaceutically acceptable salt is known to function as an antagonist and also as a biosynthesis inhibitor against leukotrienes. The sodium salt of montelukast is commercially available from Merck under the trademark of Singulair® for treating asthma.

EP 480,717 discloses a method of preparing said montelukast sodium salt: As shown in Reaction Scheme 1, methyl 1-(mercaptomethyl)cyclopropylacetate of formula (B) is coupled with the compound of formula (A) to produce the compound of formula (C) as an intermediate, and the compound of formula (C) is then hydrolyzed to obtain the free acid form thereof, followed by treating the free acid with NaOH. However, this method gives a low yield or the manufacturing cost is high.

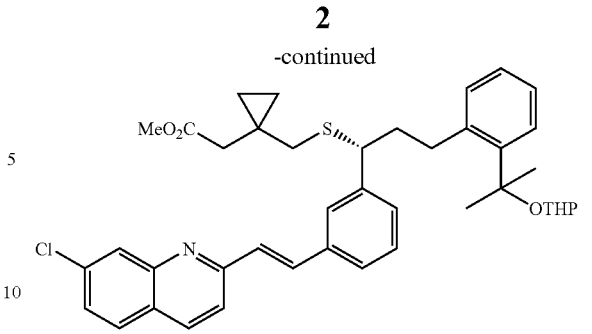

(C)

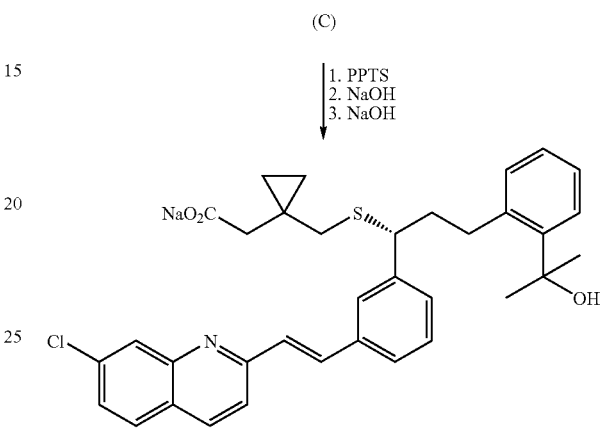

THP: tetrahydropyranyl
PPTS: Pyridinium p-toluenesulfonate

In order to solve the above-mentioned problems, EP 737,186 suggests a method as shown in Reaction Scheme 2. This method uses a methanesulfonyl compound of formula (A') having an unprotected hydroxyl group instead of the THP-protected compound of formula (A). Further, this method uses 1-(mercaptomethyl)cyclopropylacetate dilithium salt of formula (B') instead of methyl 1-(mercaptoethyl)cyclopropylacetate of formula (B), thereby making the subsequent deprotection step unnecessary. Subsequently, dicyclohexylamine is added to the compound of formula (C'') to produce the compound of formula (D), which is converted to the desired sodium salt.

Reaction Scheme 1

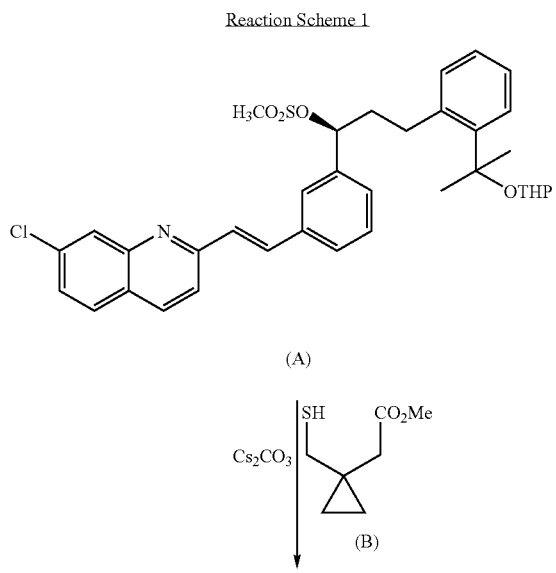

Reaction Scheme 2

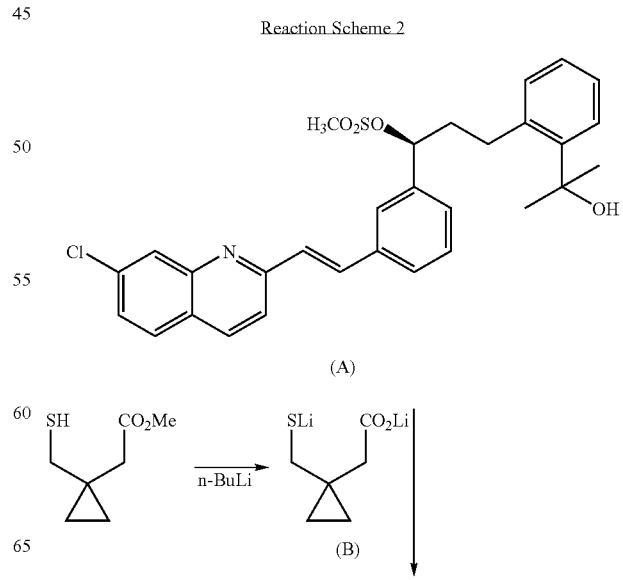

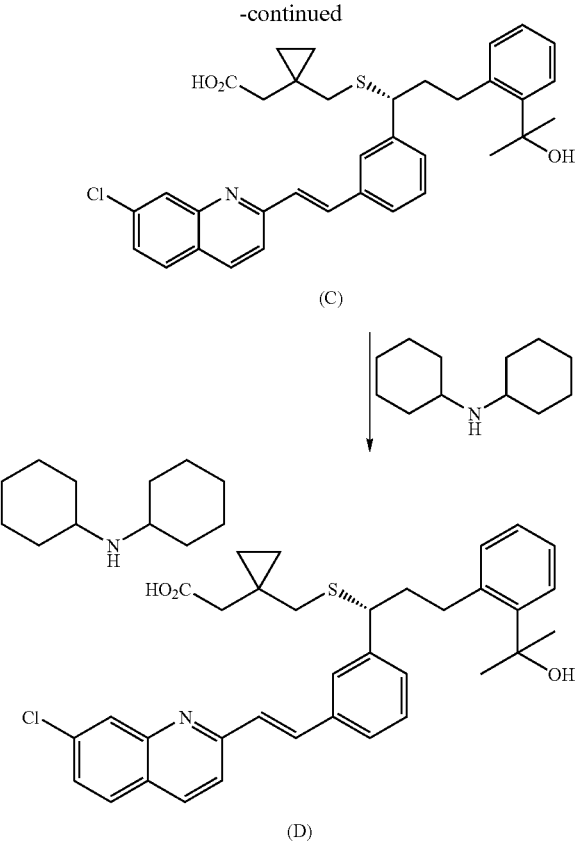

However, the methanesulfonyl compound of formula (A') used in the above process as a starting material is very unstable, which makes the whole process very complicated. Namely, the reaction to produce the compound of formula (A') must be performed at a low temperature of about −30° C. and the product is required to be kept at about −15° C. The compound of formula (A') thus produced is unstable toward moisture and air, and therefore, the reaction thereof has to be conducted quickly under carefully controlled conditions. Also, the synthesis of the compound of formula (B') requires the use of n-butyllithium which is very explosive and unstable toward moisture and air. Thus, the method described in Reaction Scheme is not suitable for large-scale production.

SUMMARY OF THE INVENTION

Accordingly, it is an object of the present invention to provide an efficient method for preparing high purity montelukast and its sodium salt in a high yield, which can be used for mass production.

It is another object of the present invention to provide a novel phosphate intermediate used in the preparation of montelukast.

In accordance with one aspect of the present invention, there is provided a method for preparing montelukast or its sodium salt of formula (I) comprising the steps of:

(a) subjecting halophosphate compound of formula (V) to a reaction with the diol compound of formula (IV) in a solvent in the presence of a base to produce a phosphate compound of formula (III); and (b) coupling the phosphate compound of formula (III) with a thiocarboxylic acid compound of formula (II) in a solvent in the presence of a base:

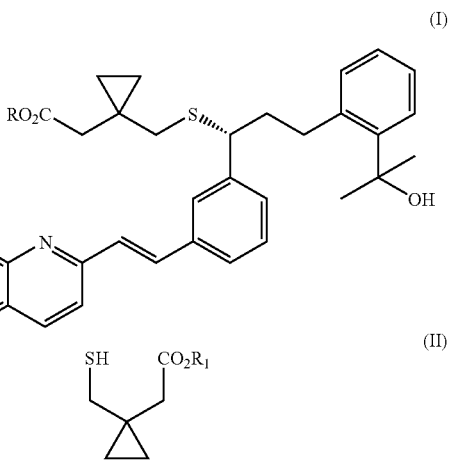

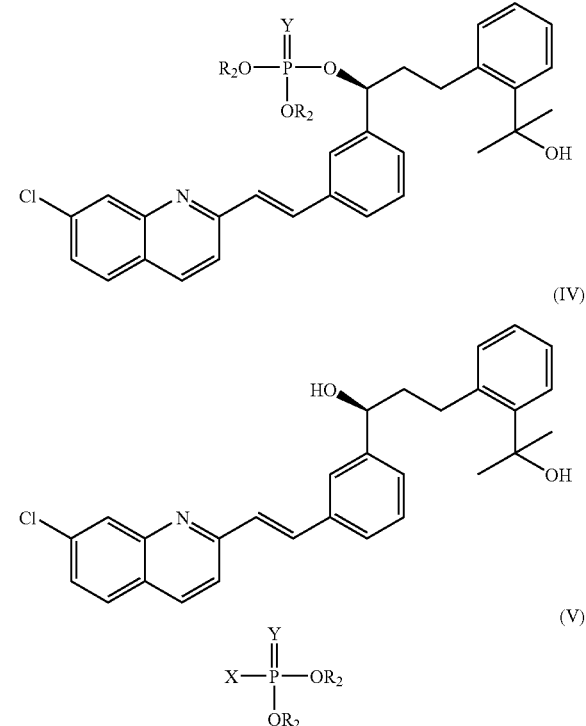

wherein,
R is H or Na;
$R_1$ is H, methyl, or ethyl;
$R_2$ is methyl, ethyl, or phenyl;
X is halogen;
Y is sulfur or oxygen.

In accordance with another aspect of the present invention, there is provided a phosphate compound of formula (III) used as an intermediate in the preparation of montelukast:

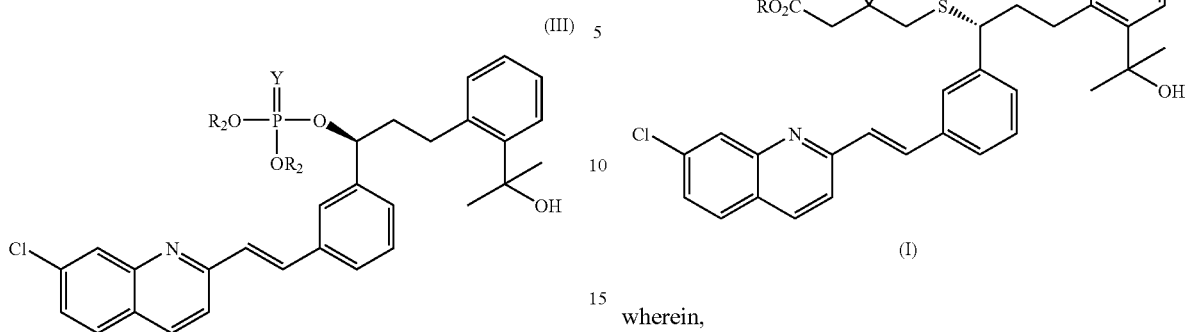

(III)

wherein,
$R_2$ is methyl, ethyl, or phenyl;
Y is sulfur or oxygen.

DETAILED DESCRIPTION OF THE INVENTION

In the present invention, the compound of formula (I) can be prepared as shown in Reaction Scheme III:

Reaction Scheme III

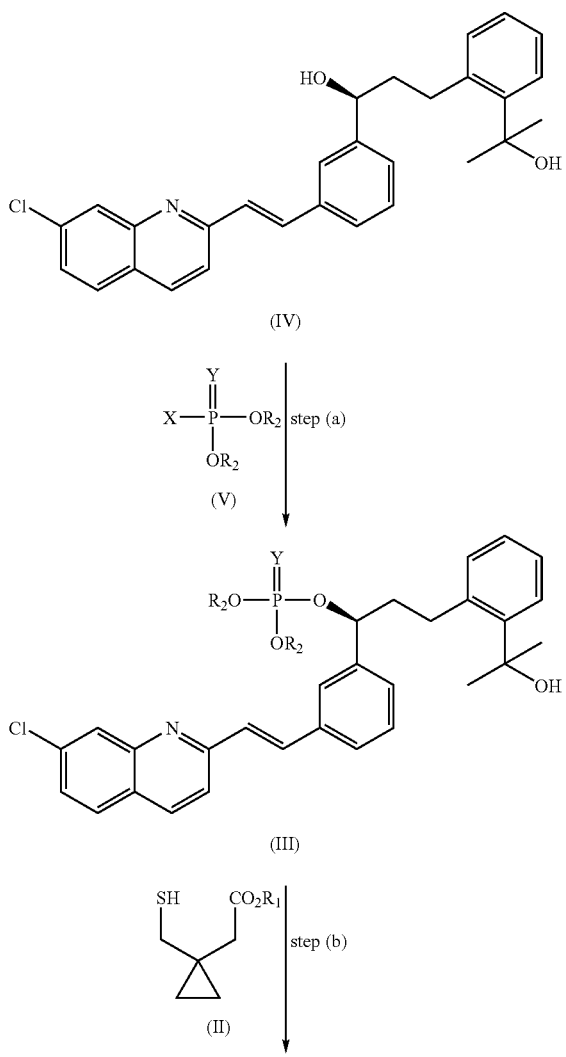

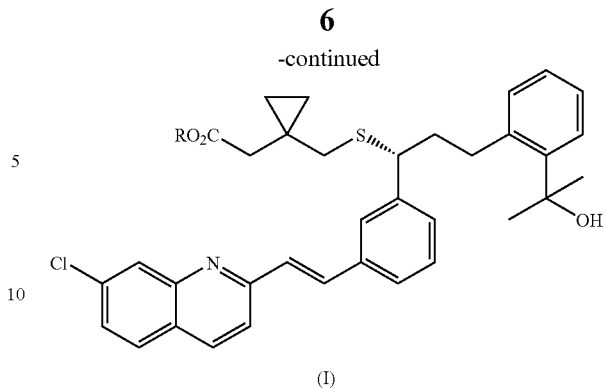

(I)

wherein,
R is H or Na;
$R_1$ is H, methyl, or ethyl;
$R_2$ is methyl, ethyl, or phenyl;
X is halogen; and
Y is sulfur or oxygen.

In the reaction step (a), the compound of formula (IV) is coupled with the halophosphate compound of formula (V) to produce the phosphate compound of formula (III) having a phosphate leaving group. The halophosphate compound of formula (V) is commercially available, or it can be easily synthesized using conventional methods. The preferred halophosphate compound of formula (V) is the compound in which X is chloro, Y is oxygen, and $R_2$ is phenyl. The most preferred phosphate leaving group is diphenylphosphate group.

In addition, the halophosphate compound (V) may be used in step (a) in an amount of 1.1 to 1.5 equivalents based on the diol compound (IV).

The acid generated during step (a) may be removed using a base selected from pyridine, triethylamine, tributylamine, diisopropylethylamine, methylpiperidine, and a mixture thereof. The preferred base is triethylamine. The base may be used in an amount of 1.2 to 2.0 equivalents based on the diol compound (IV). Also, if needed, 4-dimethylaminopyridine or 4-pyrrolidinopyridine may be used as a catalyst in step (a).

The reaction step (a) may be conducted in a solvent selected from benzene, toluene, acetonitrile, tetrahydrofuran, methylene chloride, chloroform, ethyl acetate, and a mixture thereof, preferably a mixture of toluene and methylene chloride, at a temperature ranging from −25 to 50° C.

The phosphate compound (III) obtained in step (a) may be crystallized from a solvent selected from methyl acetate, ethyl acetate, n-hexane, cyclohexane, ether, isopropylether, and a mixture thereof, preferably a mixture of ethyl acetate and n-hexane.

The phosphate compound (III) is highly stable, unlike the methanesulfonyl compound prepared by a conventional method. Generally, in order to produce a methanesulfonyl compound by the conventional method, the reaction must be conducted at about −30° C., and the product is required to be kept at about −15° C. In contrast, the phosphate compound (III) obtained according to the present invention may be kept at room temperature. Moreover, it does not undergo degradation after drying at 40° C. In addition, the phosphate compound (III) is highly pure containing only a minute amount of impurities.

In the reaction step (b), the phosphate compound of formula (III) is coupled with the thio carboxylic acid derivative of formula (II). Representative examples of the compound (II) include 1-(mercaptomethyl)cyclopropylacetic acid and its alkylesters.

In addition, the base used in step (b) may be selected from sodium hydroxide, sodium hydride, potassium t-butoxide, sodium methoxide, sodium ethoxide, triethylamine, pyridine, and a mixture thereof. The preferred base is sodium hydride. The solvent used in step (b) may be selected from dimethylformamide, dimethylsulfoxide, acetonitrile, chloroform, methylene chloride, tetrahydrofuran, 1,4-dioxane, ethyl acetate, ethanol, methanol, and a mixture thereof, with dimethylformamide being preferred.

In case 1-(mercaptomethyl)cyclopropylacetic acid is used as the compound (II) in the reaction of step (b), the amounts of 1-(mercaptomethyl)-cyclopropylacetic acid and the base used may be 2 to 4 equivalents and 3 to 5 equivalents, respectively, based on the compound of formula (III).

On the other hand, in case methyl 1-(mercaptomethyl) cyclopropylacetate is used as the compound of formula (II), the amounts of methyl 1-(mercaptomethyl)cyclopropylacetate and the base used may be 1 to 3 equivalents and 1 to 2 equivalents, respectively, based on the compound (III).

The montelukast product thus obtained may be hydrolyzed in the presence of a base such as sodium hydroxide, to obtain the sodium salt thereof. In order to produce a high-purity sodium salt of montelukast, the sodium hydroxide treatment is preferably conducted after separating the free acid form of montelukast.

As described above, the inventive method of preparing montelukast uses a novel phosphate intermediate compound instead of the methanesulfonate derivative used in the conventional method, which provides the benefits of the desired product having greatly improved stability and drastically reduced impurity. Therefore, the inventive method is suitable for producing montelukast in a large scale.

The following Examples are given for the purpose of illustration only, and are not intended to limit the scope of the invention.

Example 1

Preparation of 2-(2-(3-(S)-(3-(2-(7-chloro-2-quinolinyl)ethenyl)-phenyl)-3-diphenylphosphate oxypropyl)phenyl)-2-propanol 20 g of 2-(2-(3-(S)-(3-(2-(7-chloro-2-quinolinyl)ethenyl) phenyl)-3-hydroxypropyl)phenyl)-2-propanol was dissolved in 240 ml of a mixture of methylene chloride and toluene (2:1), and 7.31 ml (1.2 eq.) of triethylamine was slowly added thereto. To the resulting mixture, 13.6 ml of diphenylchlorophosphate and 1.06 g of 4-dimethylaminopyridine were sequentially added dropwise. After about 1 hr, the completion of the reaction was confirmed by thin layer chromatography (TLC). The reaction mixture was treated with 100 ml of methylene chloride and 200 ml of distilled water. With shaking, the organic layer was separated and dried over sodium sulfate, followed by removing the solvent under reduced pressure. The residue thus obtained was dissolved in 60 ml of a mixture of ethyl acetate and n-hexane (1:3), and the product was recrystallized therefrom. The crystallized product was filtered, washed with 40 ml of distilled water and dried to obtain 29.5 g (97.8%) of the title compound as a yellow solid.

m.p.: 127° C.

$^1$H-NMR (300 MHz, CDCl$_3$): δ 8.4 (1H, d), 7.94 (1H, d), 7.75 (3H, m), 6.97-7.35 (20H, m), 5.70-5.72 (1H, m), 3.02-3.09 (2H, m), 2.29-2.34 (2H, m), 1.65 (3H, s), 1.59 (3H, s).

Example 2

Preparation of 1-(((1-(R)-(3-(2-(7-chloro-2-quinolidyl)-ethenyl)phenyl)-3-(2-(1-hydroxy-1-methylethyl)phenyl)propyl)thio)methyl)-cyclopropylacetic acid 12.7 g of 1-(mercaptomethyl)cyclopropylacetic acid dissolved in 90 ml of dimethylformamide was slowly added to a solution of 6.26 g of 60% sodium hydride dissolved in 90 ml of dimethylformamide at 0 to 5° C. To the resulting mixture, 30 g of 2-(2-(3-(S)-(3-(2-(7-chloro-2-quinolinyl)ethenyl) phenyl)-3-diphenylphosphate oxypropyl)phenyl)-2-propanol obtained in Example 1 dissolved in 120 ml of dimethylformamide was slowly added dropwise. After the temperature was slowly increased to room temperature, the reaction was run for 18 to 20 hrs. Then, the reaction mixture was neutralized with a saturated ammonium chloride aqueous solution, and treated with ethyl acetate and distilled water. With shaking, the organic layer was separated and dried over sodium sulfate, followed by removing the solvent under reduced pressure. The residue thus obtained was dissolved in 270 ml of cyclohexane, and the product was recrystallized therefrom. The crystallized product was filtered, washed and dried to obtain 22.2 g (87.1%) of the title compound as a yellow solid.

$^1$H-NMR (300 MHz, CD$_3$OD): δ 8.27 (1H, d), 7.98 (1H, s), 7.78 (2H, d), 7.73 (2H, d), 7.38-7.56 (6H, m), 7.07-7.14 (3H, m), 4.84 (1H, t), 3.30-3.33 (1H, m), 2.84-2.87 (1H, m), 2.52 (2H, s), 2.41 (2H, s), 2.18-2.23 (2H, m), 1.55 (6H, s), 0.37-0.52 (4H, m).

Example 3

Preparation of 1-(((1-(R)-(3-(2-(7-chloro-2-quinolidyl)ethenyl)phenyl)-3-(2-(1-hydroxy-1-methylethyl)phenyl)propyl)-thio)methyl)cyclopropylacetate sodium salt Step 1: Preparation of methyl 1-(((1-(R)-(3-(2-(7-chloro-2-quinolidyl)-ethenyl)phenyl)-3-(2-(1-hydroxy-1-methylethyl)phenyl)propyl)thio)methyl)-cyclopropylacetate 2.1 g of methyl 1-(acetylthiomethyl)cyclopropylacetate dissolved in 35 ml of dimethylformamide was slowly added to a solution of 0.71 g of 60% sodium hydride dissolved in 35 ml of dimethylformamide at a temperature ranging from 0 to 5° C. To the resulting mixture, 7.73 g of 2-(2-(3-(S)-(3-(2-(7-chloro-2-quinolinyl)ethenyl)phenyl)-3-diphenylphosphate oxypropyl)phenyl)-2-propanol obtained in Example 1 dissolved in 35 ml of dimethylformamide was slowly added dropwise at a temperature ranging from 0 to 5° C. After about 1 hr, the reaction mixture was treated with ethyl acetate and distilled water. With shaking, the organic layer was separated and dried over sodium sulfate, followed by removing the solvent under reduced pressure to obtain 5.68 g (84.5%) of the title compound as a yellow liquid.

$^1$H-NMR (300 MHz, CDCl$_3$): δ 8.12 (2H, d), 7.66-7.74 (4H, m), 7.37-7.48 (6H, m), 7.12-7.20 (3H, m), 3.96 (1H, t), 3.14-3.16 (1H, m), 2.88 (1H, m), 2.53 (2H, s), 2.43 (2H, s), 1.62 (6H, d), 0.41-0.54 (4H, m).

Step 2: Preparation of 1-(((1-(R)-(3-(2-(7-chloro-2-quinolidyl)-ethenyl)phenyl)-3-(2-(1-hydroxy-1-methyl-ethyl)phenyl)propyl)thio)methyl)-cyclopropyl acetic acid 12 g of methyl 1-(((1-(R)-(3-(2-(7-chloro-2-quinolidyl) ethenyl)phenyl)-3-(2-(1-hydroxy-1-methyl-ethyl)phenyl) propyl)thio)methyl)cyclopropylacetate obtained in step 1 was dissolved in a mixture of 60 ml of tetrahydrofuran and 30 ml of methyl alcohol. After adjusting the temperature to 10 to 15° C., 24 g of 10% NaOH solution was slowly added to the resulting mixture. Then, the temperature was slowly increased to room temperature (24 to 27° C.), and the reaction mixture was stirred for 20 hrs. After reaction was completed, the organic layer was separated and dried, followed by removing the solvent under reduced pressure. The residue thus obtained was mixed with water layer again, and 120 ml of toluene was added thereto. Subsequently, the pH of the reaction product was adjusted to 4 by adding 300 ml of acetic acid. The organic layer was separated again and dried over sodium sulfate, followed by removing the solvent under reduced pressure. The residue thus obtained was dissolved in 96 ml of a mixture of isopropanol and distilled water (2:1), and the product was recrystallized therefrom. The crystallized product was filtered to obtain 9.82 g (83%) of the title compound as a yellow solid.

$^1$H-NMR (300 MHz, CD3OD): δ 8.27 (1H, d), 7.98 (1H, s), 7.78 (2H, d), 7.73 (2H, d), 7.38-7.56 (6H, m), 7.07-7.14 (3H, m), 4.84 (1H, t), 3.30-3.33 (1H, m), 2.84-2.87 (1H, m), 2.52 (2H, s), 2.41 (2H, s), 2.18-2.23 (2H, m), 1.55 (6H, s), 0.37-0.52 (4H, m).

m.p.: 154° C., purity>99%

Step 3: Preparation of 1-(((1-(R)-(3-(2-(7-chloro-2-quinolidyl)ethenyl)phenyl)-3-(2-(1-hydroxy-1-methyl-ethyl)phenyl)propyl)thio)-methyl)cyclopropylacetate sodium salt 5 g of 1-(((1-(R)-(3-(2-(7-chloro-2-quinolidyl)ethenyl)phenyl)-3-(2-(1-hydroxy-1-methyl-ethyl)phenyl)propyl)thio)methyl)cyclopropylacetic acid obtained in step 2 was mixed with 10 ml of toluene, followed by removing the solvent under reduced pressure to remove the solvent. To the residue thus obtained, 14.5 ml of toluene and 13 ml of 0.5N NaOH/MeOH solution were sequentially added. The resulting mixture was stirred for 30 min, followed by removing the solvent under reduced pressure. The residue was dissolved in 10 ml of toluene and 50 ml of n-hexane, and the product was recrystallized therefrom. The crystallized product was filtered to obtain 5.1 g (98%) of the title compound as a pale yellow solid.

$^1$H-NMR (300 MHz, CD$_3$OD): δ 8.29 (1H, d), 7.99 (1H, s), 7.83-7.91 (3H, m), 7.72 (1H, s), 7.49-7.52 (2H, m), 7.38-7.44 (4H, m), 7.10-7.15 (3H, m), 4.04 (1H, t), 3.08 (1H, m), 2.82 (1H, m), 2.66 (1H, d), 2.52 (1H, d), 2.43 (1H, d), 2.29 (1H, d), 2.16-2.24 (2H, m), 1.52 (6H, s), 0.33-0.52 (4H, m)

Comparative Example 1

Preparation of 1-(((1-(R)-(3-(2-(7-chloro-2-quinolidyl)ethenyl)phenyl)-3-(2-(1-hydroxy-1-methyl-ethyl)phenyl)propyl)-thio)methyl)cyclopropylacetate dicyclohexylamine salt Step 1: Preparation of 2-(2-(3-(S)-(3-(2-(7-chloro-2-quinolidyl)-ethenyl)phenyl)-3-methanesulfonyloxypropyl)phenyl)-2-propanol 10 g of 2-(2-(3-(S)-(3-(2-(7-chloro-2-quinolidyl)ethenyl)phenyl)-3-hydroxypropyl)phenyl)-2-propanol was added to a mixture of 28.5 ml of toluene and 71.3 ml of acetonitrile under nitrogen atmosphere. To the resulting mixture, 4.41 ml of diisopropylethylamine was added. After the temperature was decreased to −25° C., 4.41 ml of methanesulfonyl chloride was added dropwise for 30 mins to the resulting mixture, followed by stirring for about 2.5 hrs. After the temperature was decreased to −35° C., the reaction mixture was further stirred for 2 hrs to produce crystals. Then, the resulting crystals were quickly filtered and the residue was washed with acetonitrile of −30° C. and n-hexane of −5° C. The resulting product was dried through nitrogen atmosphere to obtain 8.97 g (76.7%) of the title compound. The compound thus obtained was kept in dual polypropylene pouch at −18° C.

$^1$H-NMR (300 MHz, CDCl$_3$): δ 8.11 (m, 2H), 7.69 (m, 5H), 7.41 (m, 5H), 7.19 (m, 3H), 5.70 (dd, 1H), 3.25 (m, 1H), 3.04 (m, 1H), 2.76 (s, 3H), 2.45 (m, 1H), 1.92 (s, 1H), 1.65 (s, 6H).

Step 2: Preparation of 1-(((1-(R)-(3-(2-(7-chloro-2-quinolidyl)ethenyl)phenyl)-3-(2-(1-hydroxy-1-methyl-ethyl)phenyl)propyl)thio)-methyl)cyclopropylacetate dicyclohexylamine salt 1 g of 1-(mercaptomethyl)cyclopropylacetic acid was added to 23 ml of tetrahydrofuran. After stirring for 10 mins, the resulting mixture was cooled to −15±2° C. Then, 10.6 ml of n-butyl lithium hexane solution was added thereto for 30 mins at a temperature under −5° C. to obtain slurry. The resulting slurry was left at −5±2° C. for 30 mins. Then, 3.11 g of methanesulfonate obtained in step 1 was dissolved in 14 ml of tetrahydrofuran at a temperature ranging from 0 to 5° C. to obtain a transparent lemon yellow solution. The resulting solution was transferred to the slurry for 30 mins and kept for 8.5 hrs at a temperature of −5±2° C. To the reaction mixture, a mixture of 42 ml of ethyl acetate and 42 ml of 10% NaCl solution was added to complete the reaction. After stirring for 30 mins, the organic layer was separated, sequentially washed with 27 ml of 0.5M tartaric acid and 30 ml of water 2 times, followed by concentrating under vacuum. 8 ml of the resulting product was dissolved in 38 ml of ethyl acetate. The temperature was adjusted to room temperature (20±2° C.), and 1.4 ml of dicyclohexylamine was added to the resulting solution. After seeded with dicyclohexylamine salt, the resulting mixture was left for about 1 hr to obtain dense slurry. To the resulting slurry, 85 ml of n-hexane was slowly added for 2 hrs with stirring. The resulting slurry was left at 20±2° C. overnight and filtered. The cake thus obtained was washed with 25 ml of the mixture of ethyl acetate and n-hexane (1:2) of 0±2° C., and dried at 40° C. under vacuum to obtain 1.63 g (43%) of the title compound.

$^1$H-NMR (CD$_3$OD): δ 8.25 (d, 1H), 7.95 (d, 1H), 7.86 (d, 1H), 7.83 (d, 1H), 7.77 (d, 1H), 7.70 (bs, 1H), 7.54 (d, 1H), 7.49 (d, 1H), 7.46-7.35 (m, 4H), 7.12-7.03 (m, 3H), 4.87 (s, active H), 4.03 (dd, 1H), 3.11-3.05 (m, 3H), 2.84-2.81 (m, 1H), 2.64 (d, 1H), 2.52 (d, 1H), 2.38 (d, 1H), 2.29 (d, 1H), 2.23 (m, 1H), 2.00 (m, 4H), 1.82 (m, 4H), 1.66 (m, 2H), 1.51 (2s, 6H), 1.37-1.14 (m, 10H), 0.53-0.32 (m, 4H).

While the invention has been described with respect to the above specific embodiments, it should be recognized that various modifications and changes may be made to the invention by those skilled in the art which also fall within the scope of the invention as defined by the appended claims.

What is claimed is:

1. A method for preparing montelukast or its sodium salt of formula (I) comprising the steps of:

(a) allowing a halophosphate compound of formula (V) to react with the diol compound of formula (IV) in a solvent in the presence of a base to produce a phosphate compound of formula (III); and (b) coupling the phosphate compound of formula (III) with a thiocarboxylic acid compound of formula (II) in a solvent in the presence of a base:

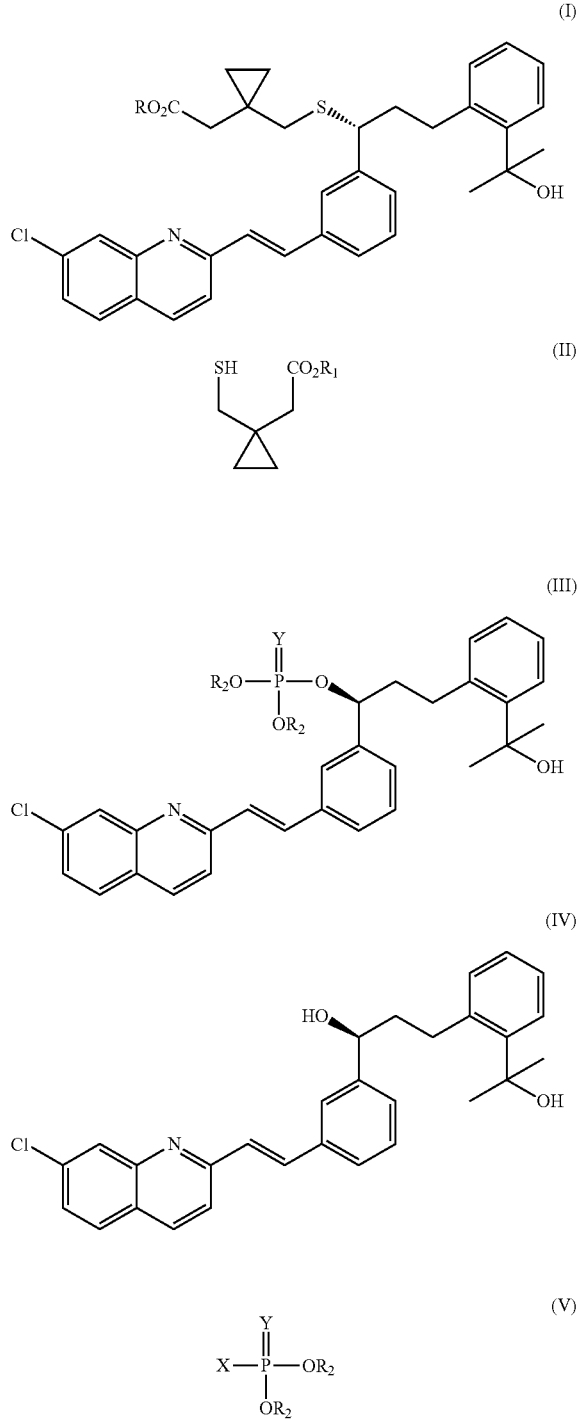

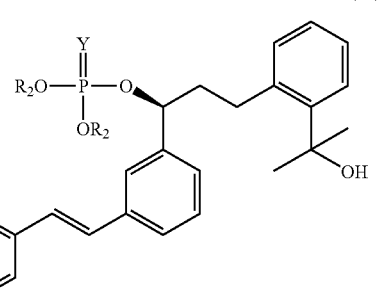

wherein,
R is H or Na;
$R_1$ is H, methyl, or ethyl;
$R_2$ is methyl, ethyl, or phenyl;
X is halogen;
Y is sulfur or oxygen.

2. The method of claim 1, wherein the base used in step (a) is selected from the group consisting of pyridine, triethylamine, tributylamine, diisopropylethylamine, methylpiperidine, and a mixture thereof.

3. The method of claim 2, wherein the base is triethylamine.

4. The method of claim 1, wherein the amount of the halophosphate compound of formula (V) used in step (a) is one equivalent or more based on the diol compound of formula (IV).

5. The method of claim 1, wherein 4-dimethylaminopyridine or 4-pyrrolidinopyridine is further used as a catalyst in step (a).

6. The method of claim 1, wherein the halophosphate compound is the compound of formula (V) in which X is Cl, Y is O, and $R_2$ is phenyl.

7. The method of claim 1, wherein the solvent used in step (a) is selected from the group consisting of benzene, toluene, acetonitrile, tetrahydrofuran, methylene chloride, chloroform, ethyl acetate, and a mixture thereof.

8. The method of claim 1, wherein the base used in step (b) is selected from the group consisting of sodium hydroxide, sodium hydride, potassium t-butoxide, sodium methoxide, sodium ethoxide, triethylamine, pyridine, and a mixture thereof.

9. The method of claim 1, wherein the solvent used in step (b) is selected from the group consisting of dimethylformamide, dimethylsulfoxide, acetonitrile, chloroform, methylene chloride, tetrahydrofuran, 1,4-dioxane, ethyl acetate, ethanol, methanol, and a mixture thereof.

10. The method of claim 9, wherein the solvent is dimethylformamide.

11. A phosphate compound of formula (III):

wherein,
$R_2$ is methyl, ethyl, or phenyl;
Y is sulfur or oxygen.

* * * * *